(12) United States Patent
Ren et al.

(10) Patent No.: US 8,836,351 B2
(45) Date of Patent: *Sep. 16, 2014

(54) CHLORIDE DETECTION

(75) Inventors: Fan Ren, Gainesville, FL (US); Stephen John Pearton, Gainesville, FL (US)

(73) Assignee: University of Florida Research Foundation, Inc., Gainesville, FL (US)

(*) Notice: Subject to any disclaimer, the term of this patent is extended or adjusted under 35 U.S.C. 154(b) by 708 days.

This patent is subject to a terminal disclaimer.

(21) Appl. No.: 12/997,163

(22) PCT Filed: Nov. 13, 2008

(86) PCT No.: PCT/US2008/083378
§ 371 (c)(1),
(2), (4) Date: Dec. 9, 2010

(87) PCT Pub. No.: WO2009/151473
PCT Pub. Date: Dec. 17, 2009

(65) Prior Publication Data
US 2011/0084713 A1    Apr. 14, 2011

Related U.S. Application Data

(60) Provisional application No. 61/060,327, filed on Jun. 10, 2008.

(51) Int. Cl.
*G01R 27/08* (2006.01)
*H01L 29/737* (2006.01)
*G01N 27/414* (2006.01)

(52) U.S. Cl.
CPC ................................. *G01N 27/414* (2013.01)
USPC ............ 324/693; 257/192; 257/194; 257/253

(58) Field of Classification Search
USPC .......... 324/693, 691, 649, 600; 257/183, 187, 257/192, 194, 195, 196, 197, 200, 253
See application file for complete search history.

(56) References Cited

U.S. PATENT DOCUMENTS

| 4,816,118 | A |   | 3/1989 | Oyama et al. |
| 4,892,834 | A | * | 1/1990 | Rauh .............................. 436/149 |
| 5,394,094 | A | * | 2/1995 | Wagner ......................... 324/556 |
| 5,610,410 | A | * | 3/1997 | Imanishi ......................... 257/76 |

(Continued)

FOREIGN PATENT DOCUMENTS

JP          58-167951 A     10/1983

OTHER PUBLICATIONS

S.C. Hung et al., "Detection of chloride ions using an integrated Ag/AgCl electrode with AlGaN/GaN high electron mobility transistors," May 14, 2008, Applied Physics Letters, 92, 193903.

(Continued)

*Primary Examiner* — Hoai-An D Nguyen
(74) *Attorney, Agent, or Firm* — Saliwanchik, Lloyd & Eisenschenk

(57) ABSTRACT

A high electron mobility transistor (HEMT) capable of performing as a chlorine sensor is disclosed. In one implementation, a silver chloride layer can be provided on a gate region of the HEMT. In one application, the HEMTs can be used for the measurement and detection of chloride in bio-sensing applications. In another application, the HEMTs can be used for the detection of chloride in water for environmental and health applications.

12 Claims, 11 Drawing Sheets

(56) References Cited

U.S. PATENT DOCUMENTS

| | | | |
|---|---|---|---|
| 6,676,752 B1* | 1/2004 | Bailey et al. | 117/104 |
| 6,787,822 B1* | 9/2004 | Nuyen | 257/198 |
| 2004/0014158 A1* | 1/2004 | Bacher et al. | 435/8 |
| 2004/0229409 A1* | 11/2004 | Chang et al. | 438/149 |
| 2007/0075339 A1* | 4/2007 | Knittel et al. | 257/253 |
| 2007/0194225 A1* | 8/2007 | Zorn | 250/306 |
| 2007/0224128 A1* | 9/2007 | Dennis et al. | 424/10.1 |
| 2008/0128753 A1* | 6/2008 | Parikh et al. | 257/194 |
| 2011/0068372 A1* | 3/2011 | Ren et al. | 257/194 |
| 2012/0267693 A1* | 10/2012 | Holm-Kennedy | 257/253 |

OTHER PUBLICATIONS

Yen-Sheng Lu et al. "Anion detection using ultrathin InN ion selective field effect transistors," May 27, 2008, Applied Physics Letters 92, 212102.

S.C. Hung et al., "Integration of Selective Area Anodized AgCl Thin Film with AlGaN/GaN HEMTs for Chloride Ion Detection," Jun. 18, 2008, Electrochemical and Solid-State Letters, 11 (9) H241-H244.

M-K Tsai et al. "Depletion-mode and enhancement-mode InGaP/GaAs δ-HEMTs for low supply-voltage applications," Jan. 10, 2002, Semiconductor Science and Technology, 17, pp. 156-160.

Youngwoo Kwon et al., "Striped-Channel InAlAs/InGaAs HEMT's with Shallow-Grating Structures," Dec. 12, 1996, IEEE Transaction on Electron Devices, vol. 43, No. 12, pp. 2046-2052.

R. Grundbacher et al., "AlGaAs/InGaAs PHEMTs With Asymmetrically Recessed Gates Achieved Through a Four Layer Resist Process," Dec. 1997, Brazilian Journal of Physics, vol. 27/A, No. 4, pp. 130-133.

A. Bouloukou et al., "Novel high-breakdown InGaAs/InAlAs pHEMTs for radio astronomy applications," 2006, 7th MINT Millimeter-Wave Int. Symp., Finland, pp. 221-226.

R. Magno et al., "Low-Power, High-Speed Sb-based HEMTs and HBTs," 2004, The Electrochemical Society, Inc., Abs. 281, 205$^{th}$ Meeting.

Steven M. Currie et al., "Proton Tolerance of InAs Based HEMT and DHBT Devices," Jul. 2006, IEEE, Radiation Effects Data Workshop, pp. 66-71.

* cited by examiner

Final Metal

Gate deposition

Anodization

Final device

CHLORIDE DETECTION

CROSS-REFERENCE TO RELATED APPLICATIONS

This application is the U.S. national stage application of international Patent Application No. PCT/US2008/083378, filed Nov. 13, 2008, which claims priority to U.S. Provisional Application Ser. No. 60/060,317 61/060,327, filed Jun. 10, 2008, which are hereby incorporated by reference in their entirety.

GOVERNMENT SUPPORT

This invention was made with government support under Grant No. N000140710982 awarded by the Office of Naval Research (ONR). The government has certain rights in the invention.

BACKGROUND OF INVENTION

Chlorine is widely used in the manufacture of many products and items directly or indirectly, i.e. in paper product production, antiseptic, dye-stuffs, food, insecticides, paints, petroleum products, plastics, medicines, textiles, solvents, and many other consumer products. Chlorine is a poisonous gas that is soluble in water. It is used to kill bacteria and other microbes in drinking water supplies and waste water treatment. However, excess residual chlorine in the water also reacts with organics and forms toxic chemicals and carcinogens, such as the carcinogenic chloroform and trichloromethane. Thus, to ensure the safety of public health, it is very important to accurately and effectively monitor chlorine residues, typically in the form of chloride ion concentration, during the treatment and transport of drinking water.

In addition, in the body, chlorine exists primarily as the chloride ion. The chloride ion is an essential mineral for humans, and is maintained to a total body chloride balance in body fluids such as serum, blood, urine, exhaled breath condensate etc., by the kidneys. Chloride can be found in the body mainly in the extracellular fluid along with sodium. Some of the body chloride is found inside the cells, with the highest amounts within the red blood cells. As one of the mineral electrolytes, chloride works closely with sodium and water to help the distribution of body fluids. Chloride is easily absorbed from the small intestine. It is eliminated through the kidneys, which can also retain chloride as part of their finely controlled regulation of acid-base balance. Chloride is also found along with sodium in perspiration. Variations in the chloride ion concentration in serum may serve as an index of renal diseases, adrenalism, and pneumonia. Thus, the measurement of this parameter is clinically important. Several analytical methods, such as colorimetry, ion-selective electrodes, activation analysis, X-ray fluorescence spectrometry, and ion chromatography, have been used for the analysis of chloride in various samples. However, these methods are not portable and require expensive instrumentation. Accordingly, an accurate and fast determination of the inorganic ion content of various aqueous samples at low detection limits is of great interest.

BRIEF SUMMARY

Embodiments of the present invention relate to a high electron mobility transistor (HEMT) capable of performing chloride detection. According to an embodiment, the HEMT can be used for the detection of chloride in environment applications. In another embodiment, the HEMT can be used for the detection of chloride for medical applications.

In an embodiment, a chloride recognition layer can be provided on a gate region of the HEMT. In one specific embodiment, Ag/AgCl can be provided on the gate region of the HEMT to detect $Cl^-$ ions. In another specific embodiment, InN can be provided on the gate region of the HEMT to detect $Cl^-$ ions.

According embodiments of the disclosed sensors, a portable, low cost, continuous Cl ion monitor can be provided for environmental and medical applications.

Embodiments of the disclosed sensors can be integrated with a wireless transmitter for monitoring and reporting.

Embodiments of the subject chloride sensor can provide accurate and fast determination of the inorganic ion content of various aqueous samples at low detection limits.

DETAILED DISCLOSURE

Embodiments of the present invention provide design and fabrication of chemically functionalized high electron mobility transistor (HEMT) devices for chloride sensing. Specific sensitivity can be achieved by employing a chloride sensitive layer on the gate area of the HEMT. In an embodiment, the chloride sensitive layer can include a metal chloride. In one embodiment, the metal chloride can include silver-chloride. In another embodiment, the chloride sensitive layer can be indium nitride.

The AlGaN/GaN HEMT is an exemplary HEMT that can be used for chloride sensing. AlGaN/GaN HEMTs have high electron sheet carrier concentration channel induced by both piezoelectric polarization and spontaneous polarization. Unlike conventional semiconductor field effect transistors, the intentional dopant does not need to be included in the AlGaN/GaN HEMT structure. Instead, electrons in the two-dimensional electron gas (2DEG) channel are located at the interface between the AlGaN layer and GaN layer. In addition, there are positive counter charges at the HEMT surface layer induced by the 2DEG. Slight changes in the ambient can affect the surface charge of the HEMT, thus changing the 2DEG concentration in the channel.

HEMTs can operate over a broad range of temperatures and form the basis of next-generation microwave communication systems. Accordingly, embodiments of the present invention can be implemented as an integrated sensor/wireless chip.

Embodiments utilizing the HEMT sensor can provide a fast response time. In a further embodiment, the subject device can be used as a wireless based sensor to send testing results to a display or separate device.

Figure 1A:
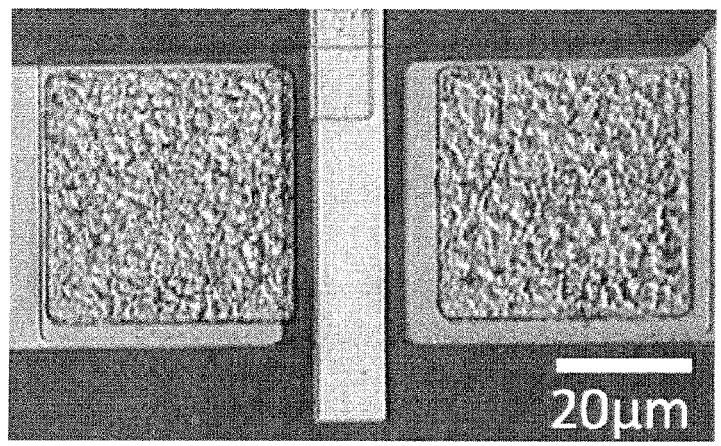
FIG. 1A shows a plan view photomicrograph of a Ag/AgCl gated AlGaN/GaN HEMT according to an embodiment of the present invention.
Figure 1B:
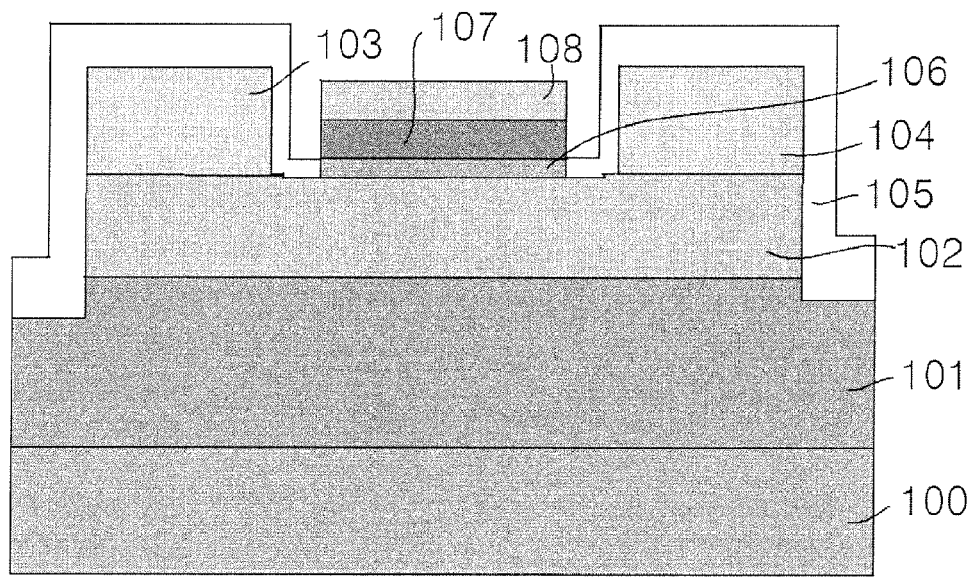
FIG. 1B shows a schematic cross sectional view of a Ag/AgCl gated HEMT according to an embodiment of the present invention.

Referring to FIG. 1B, a chloride sensor can include an HEMT formed on a substrate 100. An electrode can be formed on the gate region of the HEMT. The electrode can include a titanium (Ti) thin film 106 and a silver (Ag) thin film 107. Then, a chloride selective film 108 can be provided on the electrode. The chloride selective film can be silver chloride (AgCl). By forming the silver thin film for the electrode, the silver chloride can be formed through selective area potentiostatic anodization. The HEMT can be an AlGaN/GaN HEMT formed as a GaN layer 101 and an AlGaN layer 102 on a silicon substrate 100. A source electrode 103 and a drain electrode 104 can be disposed on the AlGaN layer 102. In a further embodiment, a passivation layer 105 can be provided to encapsulate the source and drain regions 103 and 104.

An HEMT with a Ag/AgCl gate can exhibit significant changes in channel conductance upon exposing the gate region to various concentrations of chloride ion solutions. The Ag/AgCl gate electrode changes electrical potential when it encounters chlorine ions. This gate potential changes lead to a change of surface charge in the gate region of the HEMT, inducing a higher positive charge on the AlGaN 102 surface, and increasing the piezo-induced charge density in the HEMT channel. These anions create an image positive charge on the Ag gate metal 107/108 for the required neutrality, thus increasing the drain current of the HEMT. Embodiments of the present invention can use these behaviors to provide a chloride sensing device.

Figure 1C:
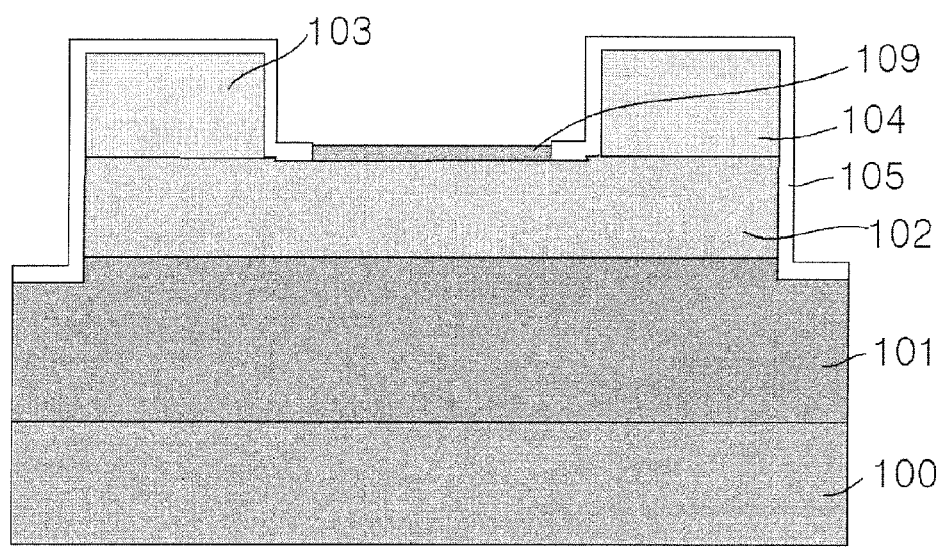
FIG. 1C shows a schematic cross sectional view of an InN gated HEMT according to an embodiment of the present invention.

Referring to FIG. 1C, according to another embodiment, a chloride sensor can include an HEMT formed on a substrate 100. A chlorine selective film 109 can be provided on the gate region of the HEMT. The HEMT can be an AlGaN/GaN HEMT formed as a GaN layer 101 and an AlGaN layer 102 on a silicon substrate 100. A source electrode 103 and a drain electrode 104 can be disposed on the AlGaN layer 102. In a further embodiment, a passivation layer 105 can be provided to encapsulate the source and drain regions 103 and 104. According to an embodiment, an indium nitride (InN) layer 109 can be epitaxially grown on the surface of the AlGaN layer 102 in the gate area of the HEMT. The positively charged surface donor states of the InN layer allow negatively charged chlorine ions to be selectively attracted to the InN surface. The presence of chlorine creates a potentiometric response from the InN layer, which in turn affects the current of the HEMT.

In one embodiment, the InN layer can be grown on the AlGaN surface using a molecular-beam epitaxy system equipped with a radio frequency (RF) nitrogen plasma source. InN epilayers can be grown by a two-stage growth method using an aluminum nitride (AlN) buffer layer on the surface of the AlGaN layer in the gate region of the HEMT.

Embodiments of the subject sensors can be used to measure chloride ion concentration in water.

In addition, embodiments of the subject sensors can be used for measurement of analytes and other bio-sensing applications.

In an embodiment, the subject chlorine sensor can be recycled. For example, the chloride sensor can be used for multiple chlorine tests by performing a resetting operation. The resetting operation can be a de-ionized (DI) water rinse.

Advantageously, in certain embodiments utilizing a 20 μm×50 μm gate sensing area, the subject sensor can sense chloride having a $1\times10^{-8}$ M concentration in a sample. Of course, embodiments are not limited to this size of a gate sensing area and can be provided to achieve test results having even more sensitivity.

Although the HEMT for the aforementioned embodiments (and example provided below) has been described as an AlGaN/GaN HEMT, other HEMTs, such as an AlGaAs/GaAs HEMT, an InGaP/GaAs HEMT, or an InAlAs/InGaAs HEMT can be used in place of the AlGaN/GaN HEMT. Furthermore, although the HEMT has been described as being grown on a silicon substrate, other substrates, such as sapphire and SiC can be utilized.

All patents, patent applications, provisional applications, and publications referred to or cited herein are incorporated by reference in their entirety, including all figures and tables, to the extent they are not inconsistent with the explicit teachings of this specification.

It should be understood that the examples and embodiments described herein are for illustrative purposes only and that various modifications or changes in light thereof will be suggested to persons skilled in the art and are to be included within the spirit and purview of this application.

EXAMPLES

The HEMT structures used for the following examples have a 2 μm thick undoped GaN buffer and a 250 Å thick undoped $Al_{0.25}Ga_{0.75}N$ cap layer. FIGS. 5A-5F illustrate the process sequence used to form the Ag/AgCl gated electrode AlGaN/GaN HEMT sensor according to embodiments of the present invention. The epi-layers were grown by metal-organic chemical vapor deposition on a 100 mm (111) Si substrate. The sheet carrier concentration was $\sim1\times10^{13}$ cm$^{-2}$ with a mobility of 980 cm$^2$/V-s at 300K. Mesa isolation was performed by Inductively Coupled Plasma (ICP) etching with $Cl_2$/Ar based discharge at −90V dc self-bias, ICP power of 300 W at 2 MHz and a process pressure of 5 mTorr. Ohmic contacts, each having an area of 50×50 μm$^2$ and separated with gaps of 20 μm, were formed of e-beam deposited Ti/Al/Pt/Au patterned by lift-off. The contacts were annealed at 850° C. for 45 seconds under flowing $N_2$ ambient. E-beam deposited Ti/Au based metallization was used for the final metal interconnections. Ti (10 nm)/Ag (100 nm) thin film was deposited as the gate metal. The titanium can improve the adhesion of the silver to the nitride surface of the gate region of the HEMT. Then, a photolithography process was performed using an AZ resist to open a window on the Ti/Ag thin film for AgCl potentiostatic anodization.

For the first set of examples, prior to anodization, samples were cleaned with acetone, isopropanol and DI water. The selective area Ag was anodized in 0.1 N HCl solution stirred continuously at 25° C. with a constant bias voltage of 1V for 5 seconds. According to these examples, only a part of the Ag thin film was anodized into AgCl. The AgCl thickness was measured to be 320 nm with scanning electron microscopy (SEM). A 500 nm thick polymethyl methacrylate (PMMA) was used to encapsulate the source/drain regions, with only the Ag/AgCl gate region opened using e-beam lithography. A plan view photomicrograph and a schematic device cross sectional view of the Ag/AgCl gated HEMT are shown in FIGS. 1A and 1B.

For the second set of examples, after performing the photolithography process, a portion of the Ti/Ag thin film was exposed for anodization and a platinum foil was used as the counter electrode. The anodization was conducted with 0.1N HCl electrolyte stirred continuously at room temperature at 1 V for 10 seconds at a frequency of 1 Hz. At the anode electrode, Ag reacted with hydrogen chloride and formed AgCl as the following half-cell equation: $2 Ag+2HCl \rightarrow 2 AgCl+2H^{+}+2e^{-}$. Hydrogen bubbles formed at the reference Pt electrode. After anodization, the samples were rinsed with DI-water and dried with filtered nitrogen. The same thickness of Ti/Ag layers was also deposited on Si (100) samples, which were used to study the anodization rate and composition of the anodized films. An Agilent 4156C parameter analyzer was utilized to supply constant DC voltage and also monitor the current during anodization.

The first set of example tests illustrates the effect of exposing the gate region of Ag/AgCl gated GaN/AlGaN HEMTs with different concentrations of $Cl^-$ ion solutions. The sensitivity, the temporal resolution, and the limit of detection (LOD) of the HEMT sensor for $Cl^-$ ion detection were also studied. The effects of chlorine concentration on sensing sensitivity were investigated using the above described devices. For these examples, the drain current characteristics of the HEMT sensor were measured at 25° C. using Agilent 4156C parameter analyzer when the gate region was exposed to water and different concentrations of NaCl solutions.

Figure 2A:
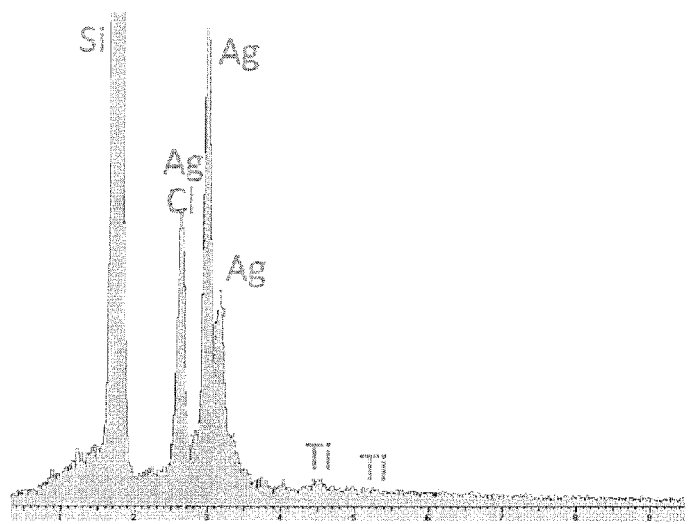
FIG. 2A shows an energy dispersive spectroscopy spectrum of anodized AgCl thin film.
Figure 2B:
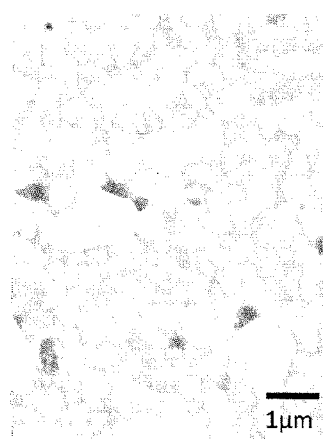
FIG. 2B shows a SEM image of AgCl before anodization.
Figure 2C:
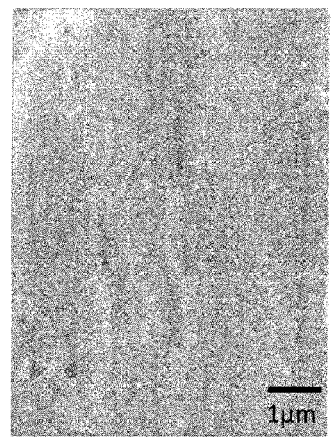
FIG. 2C shows a SEM image of AgCl after anodization.

The composition of the as-prepared Ag/AgCl thin film was characterized using energy dispersive x-ray spectroscopy (EDS) with a silicon substrate deposited with the same Ti (10 nm)/Ag (100 nm) thin film as on the gate area of the HEMT sample. There were Ag, Cl, Ti and Si signals detected with EDS, as shown in FIG. 2A. The atomic ratio of Cl to Ag was estimated to be 0.35 to 0.65, consistent with the intentional partial anodization of the Ag thin film. The signals for Ti and Si element in the EDS spectrum were attributed to the Ti adhesion layer under the Ag thin film and the silicon substrate. FIGS. 2B and 2C show the surface morphology of the Ag thin film before anodization and the AgCl layer after anodization, respectively, for the first set of examples. The grain size and the anodization rate of the AgCl appear to depend on the applied bias voltage during the anodization process.

Figure 3:
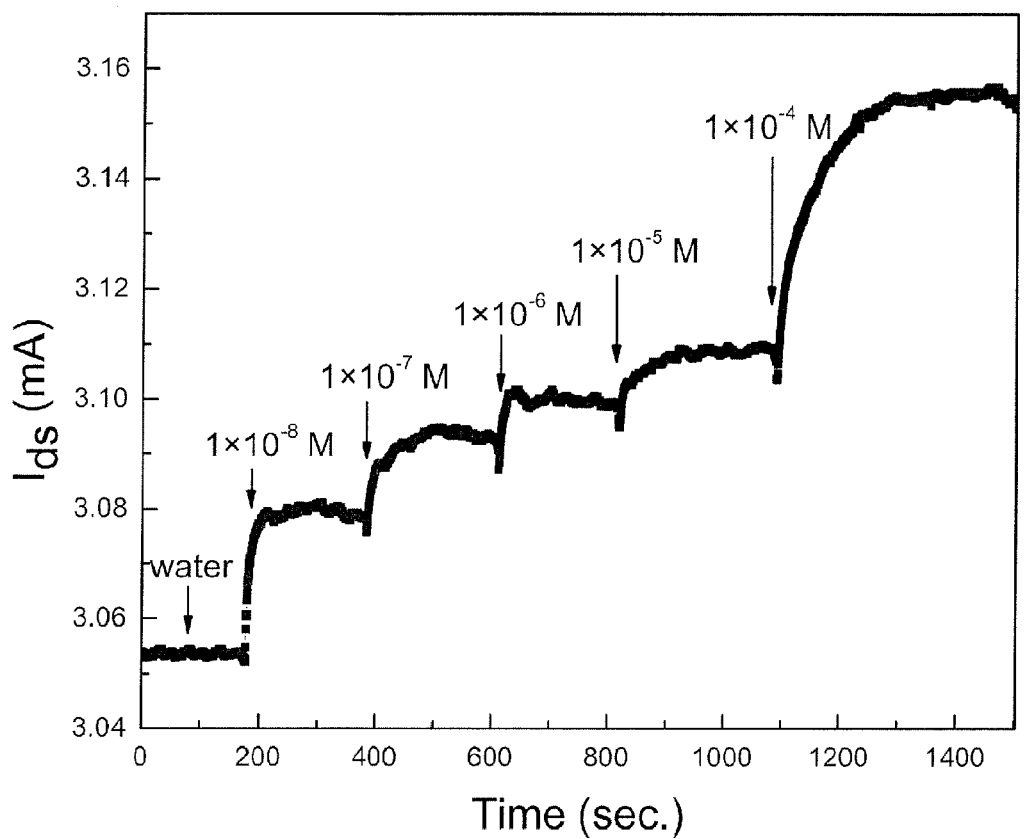
FIG. 3 shows a time-dependent drain current of a Ag/AgCl gated AlGaN/GaN HEMT exposed to different concentrations of NaCl solutions according to an embodiment.

FIG. 3 shows the time dependence of Ag/AgCl HEMT drain current at a constant drain bias voltage of 500 mV during exposure to solutions with different chlorine ion concentrations. The HEMT sensor was first exposed to DI water. Here, no change of the drain current was detected with the addition of DI water at 100 seconds. This stability indicates that noise from the mechanical change of the NaCl solution can be excluded. By sharp contrast, there was a rapid response of HEMT drain current observed in less than 30 seconds when a target of $1 \times 10^{-8}$ M NaCl solution was switched to the surface at 175 seconds. The abrupt current change due to the exposure of chlorine in NaCl solution stabilized after the chlorine thoroughly diffused into the water to reach a steady state. When Ag/AgCl gate metal encountered chlorine ions, the electrical potential of the gate was changed, inducing a higher positive charge on the AlGaN surface, and increased the piezo-induced charge density in the HEMT channel. Then, $1 \times 10^{-7}$ M of NaCl solution was applied at 382 seconds. As shown in FIG. 3, the addition was accompanied with a larger signal corresponding to the higher chlorine concentration. Further real time tests were carried out to explore the detection of higher $Cl^-$ ion concentrations. The sensors were exposed to $10^{-8}$ M, $10^{-7}$ M, $10^{-6}$ M, $10^{-5}$ M, and $10^{-4}$ M solutions continuously. The tests were also repeated five times to obtain the standard deviation of source-drain current response for each concentration. The limit of detection of this test device was $1 \times 10^{-8}$ M chlorine in DI-water. Between each test, the device was rinsed with DI water. According to these results, embodiments of the subject HEMT sensors can be made recyclable with a simple DI water rinse.

Figure 4:
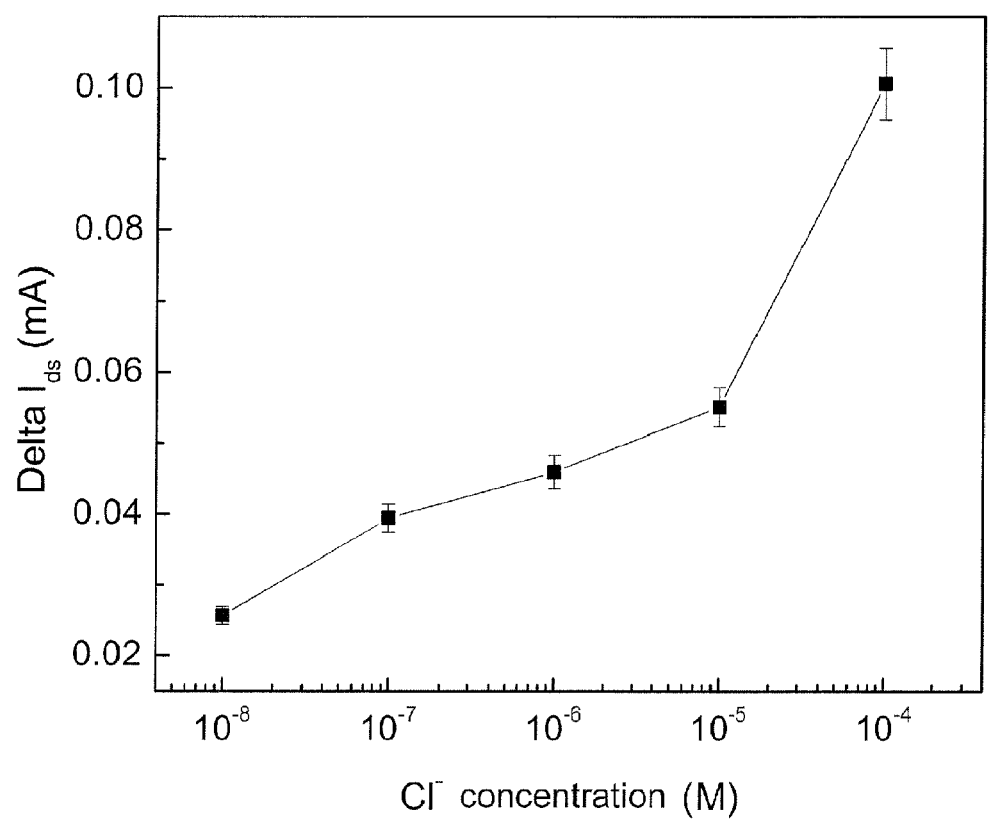
FIG. 4 shows a plot of drain current change of a Ag/AgCl gated AlGaN/GaN HEMT as a function of chloride concentration according to an embodiment.
Figure 5A:
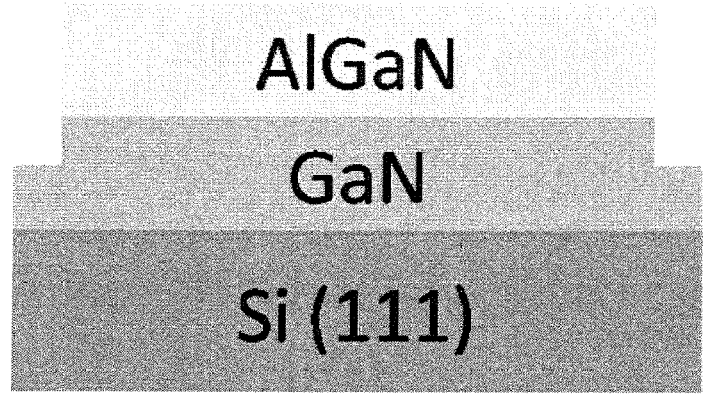
FIGS. 5A-5F show cross-sectional views illustrating a process sequence of fabricating an AlGaN/GaN HEMT sensor with an Ag/AgCl gated electrode according to an embodiment.
Figure 5B:
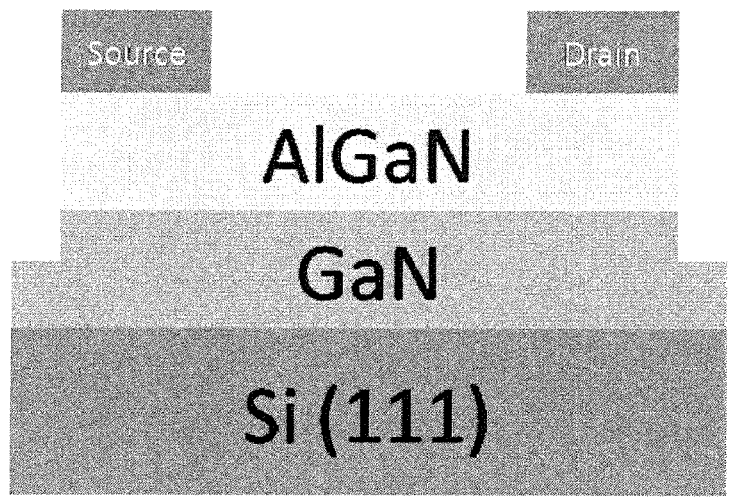
Figure 5C:
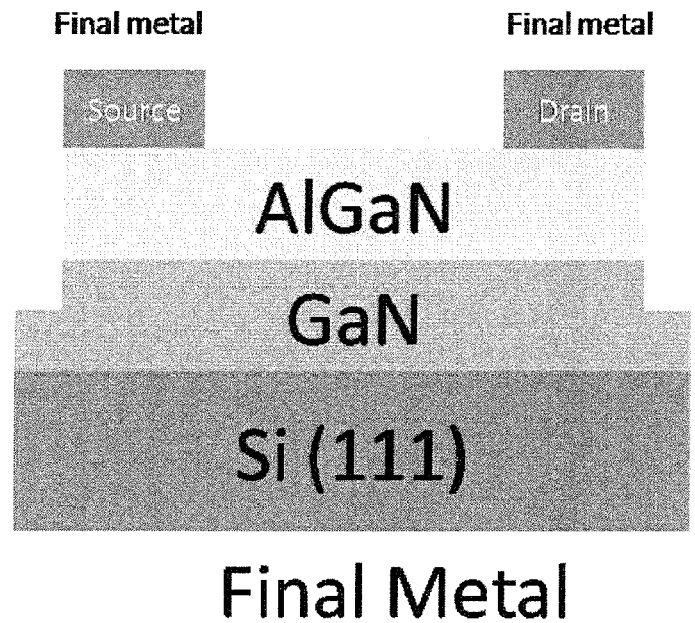
Figure 5D:
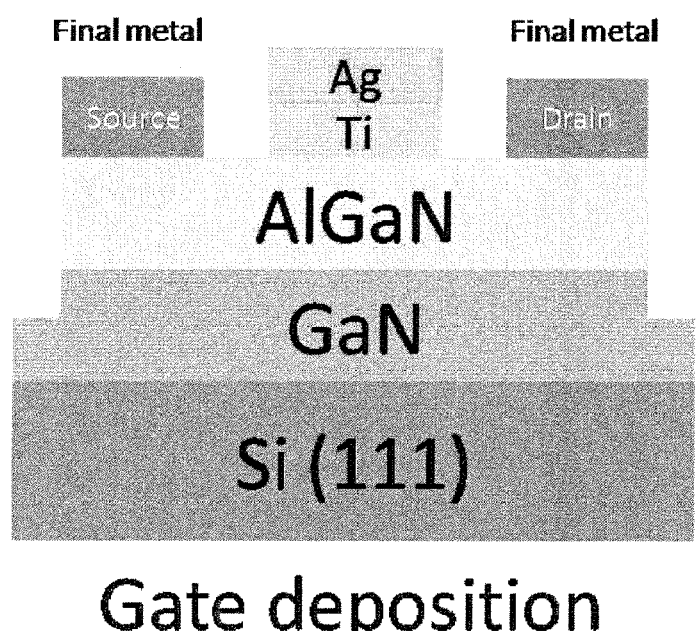
Figure 5E:
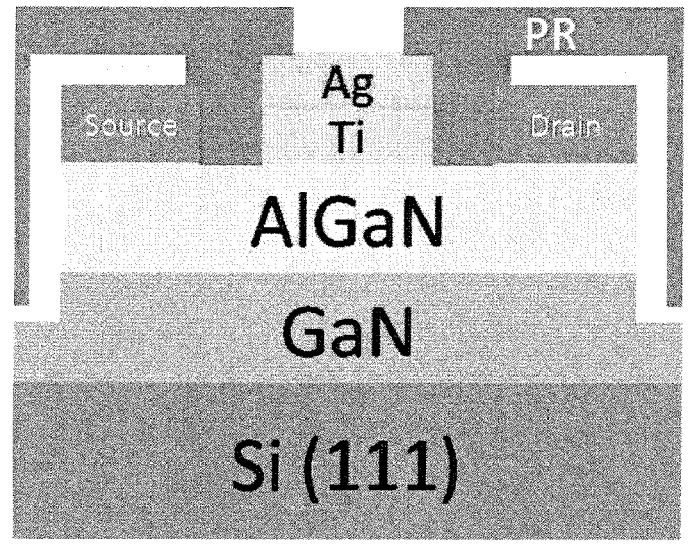
Figure 5F:
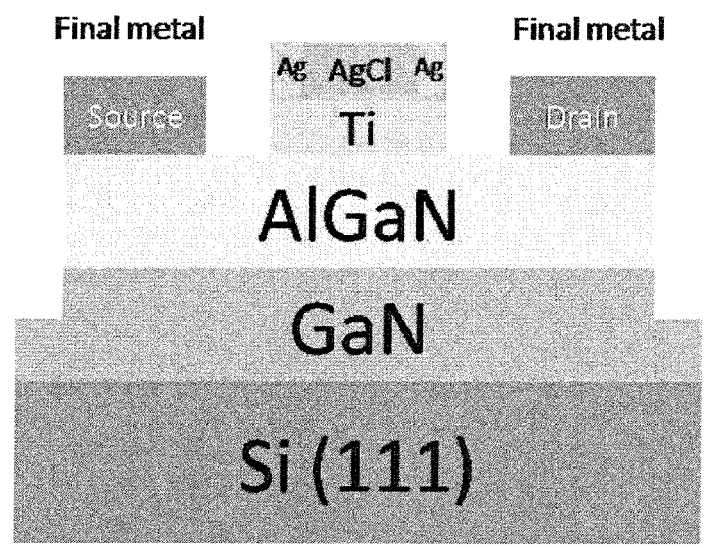

FIG. 4 shows the drain current change of Ag/AgCl gated HEMT as a function of the $Cl^-$ ion concentration. As illustrated by FIG. 4, the presence of the Ag/AgCl gate leads to a logarithmic dependence of current on the concentration of NaCl. According to embodiments, the subject sensor can be used for measurements of analytes. This electronic approach can be used to supplement methods such as enzyme immunoassay (EIA) and enzyme-linked immunosorbent assay (ELISA) for the measurements of analytes.

As described above, the compositions of the anodized Ag/AgCl thin film were characterized using EDS, where FIG. 2A shows the EDS spectrum of the AgCl film on the Si substrate anodized at 1 V for 10 seconds. The normalized atomic ratios of Cl to AgCl for anodized films at three different supplied voltages during the anodization process are listed in Table I.

TABLE I

|  | 1 sec. | 2 sec. | 4 sec. | 8 sec. | 16 sec. | 32 sec. | 64 sec. |
| --- | --- | --- | --- | --- | --- | --- | --- |
| 0.5 V | 11.92% | 10.25% | 14.63% | 14.63% | 40.27% | 39.65% | 41.9% |
| 1 V | 19.35% | 38.59% | 40.27% | 41% | 42.99% | 41.77% | 40.87% |
| 5 V | 42.99% | 41.07% | 41.6% | 43.36% | 43.54% | 43.54% | 41.07% |

All the anodized films show slightly chloride deficiency. The composition of the AgCl film anodized at 5V stayed constant, within the EDS measurement error of 5%, throughout the entire monitored time, indicating the completion of anodization process was achieved in less than 1 sec. By contrast, it took 16 seconds and 4 seconds for the anodization process to reach constant composition of anodized AgCl films for the samples biased at 0.5 and 1V, respectively.

Figure 6:
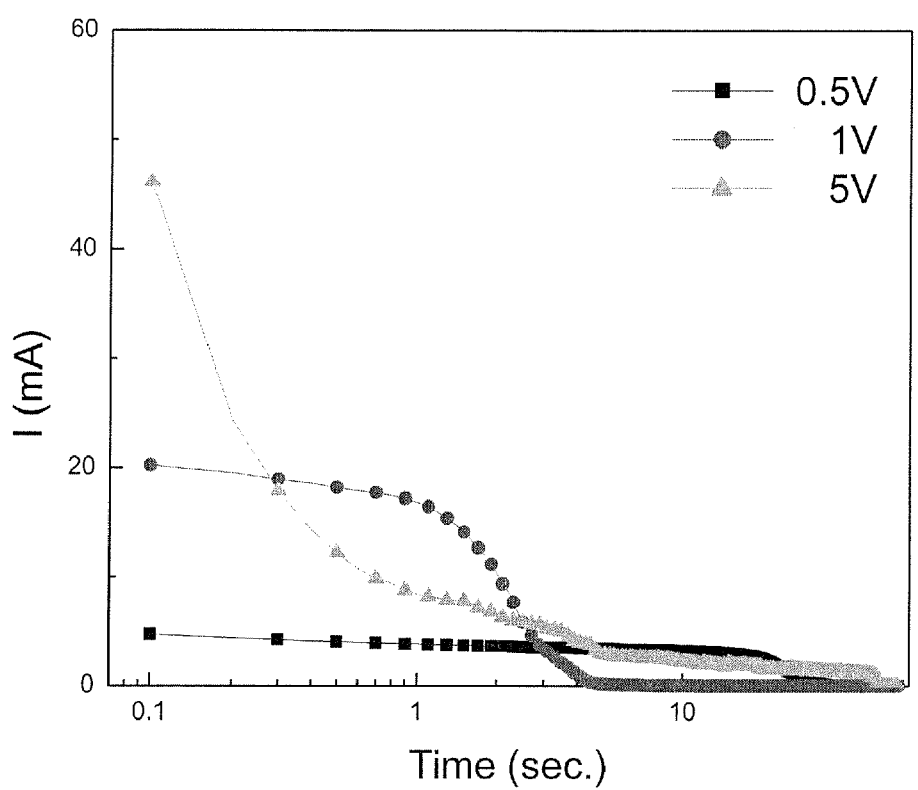
FIG. 6 shows a plot of time dependent potentiostatic behaviors of AgCl films anodized at 0.5V, 1V and 5V.

Time dependent potentiostatic behaviors of AgCl films anodized at 0.5V, 1V and 5V, are shown in FIG. 6. Higher current provided higher anodization rate, and the anodization rate increased with higher supplied voltage. The anodization rate at a voltage of 5V decreased significantly within a few seconds. This is consistent with the EDS analysis listed in Table I that there was almost no change of composition of the AgCl layer after a couple of seconds. For the anodization at 0.5 V and 1 V, there was a constant current plateau observed in the beginning of the anodization. This was due to the anodization starting at the top surface of the Ag thin film. The Ag layer provided a low resistance path for the electrons. Once the Ag layer was gradually consumed and eventually became discontinuous, the anodization current and rate decreased considerably. The length of the plateau for the condition of 0.5 V supplied voltage was much longer than the process with 1 V applied due to slower anodization rate. These rate changes of the anodization process at 0.5 V and 1 V were also consistent with the chloride composition changes shown in Table I.

Figure 7:
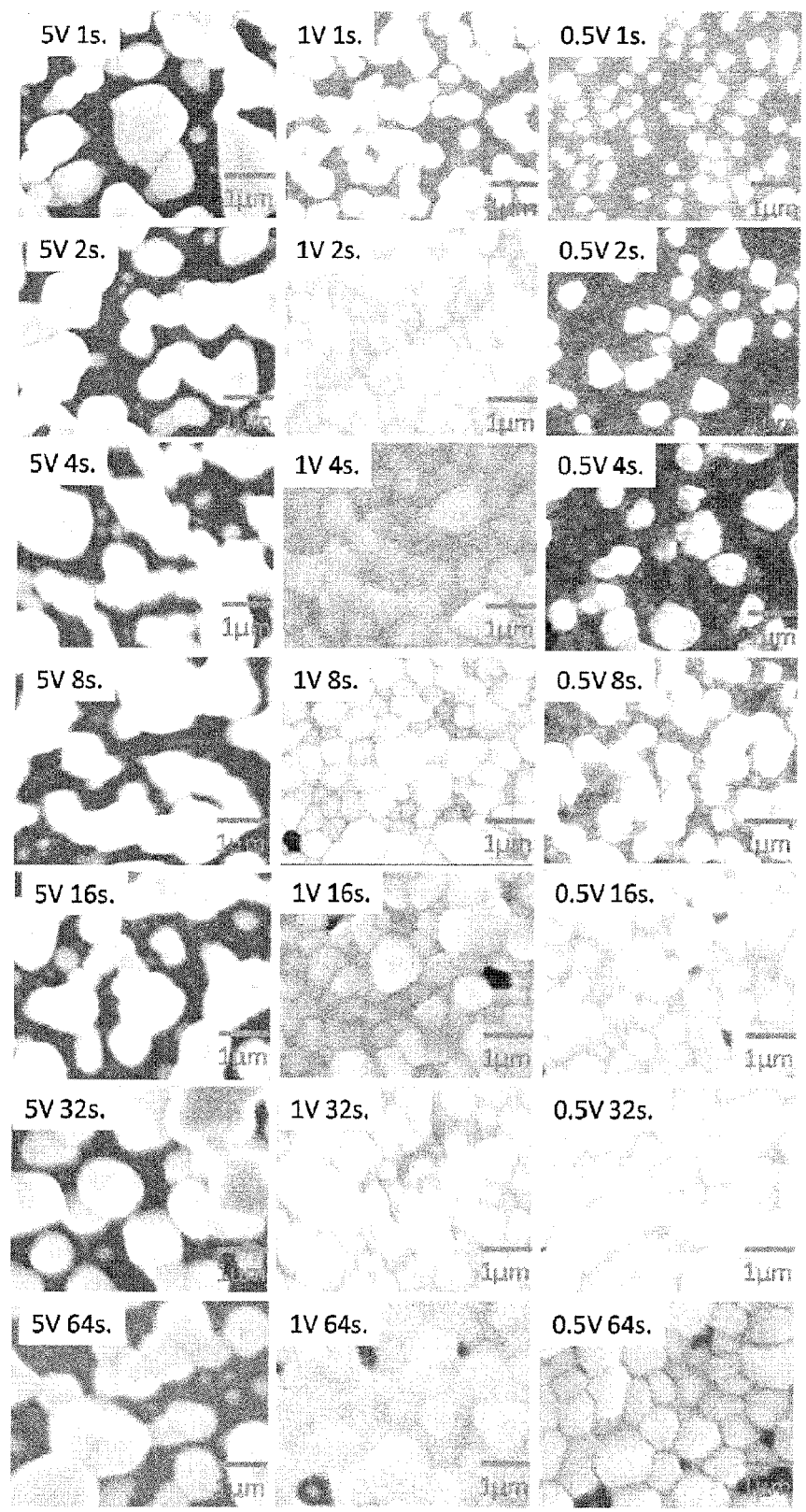
FIG. 7 shows SEM images of anodized AgCl film surface morphologies at different stages of the anodization process in accordance with an embodiment; the left column represents a surface anodized with the bias voltage of 5 V, the middle column represents a surface anodized with the bias voltage of 1 V, and the right column represents a surface anodized with the bias voltage of 0.5 V.

The scanning electron microscopy (SEM) pictures of anodized AgCl film surface morphologies at different stages of the anodization process are illustrated in FIG. 7. The left column shows the surface morphologies of anodized films with bias voltage of 5 V during the anodization. There was no obvious change of the surface morphology observed for the entire anodization process. The grain size of the AgCl was around 500 nm, which was much larger than those anodized at 0.5 V or 1 V. The grains were separate from each other and no apparent grain growth occurred in the period after 1 second of the anodization process. This observation is consistent with the fairly constant chloride composition in the AgCl film in Table I. The middle column in FIG. 7 shows surface morphologies of the anodized films with bias voltage of 1 V. There was no obvious change after 2 seconds of the anodization process. However, the grain size of the anodized AgCl film with the bias voltage of 1 V was smaller than the films anodized at 5 V. The grains form a continuous film. The right column in FIG. 7 shows the surface morphology of the films anodized at 0.5 V. There was grain growth observed in the early stages of the anodization. After the 16 seconds of the anodization, the grain growth stopped and the AgCl film became continuous. This result was also consistent with the chloride composition changes shown in Table I.

Figure 8:
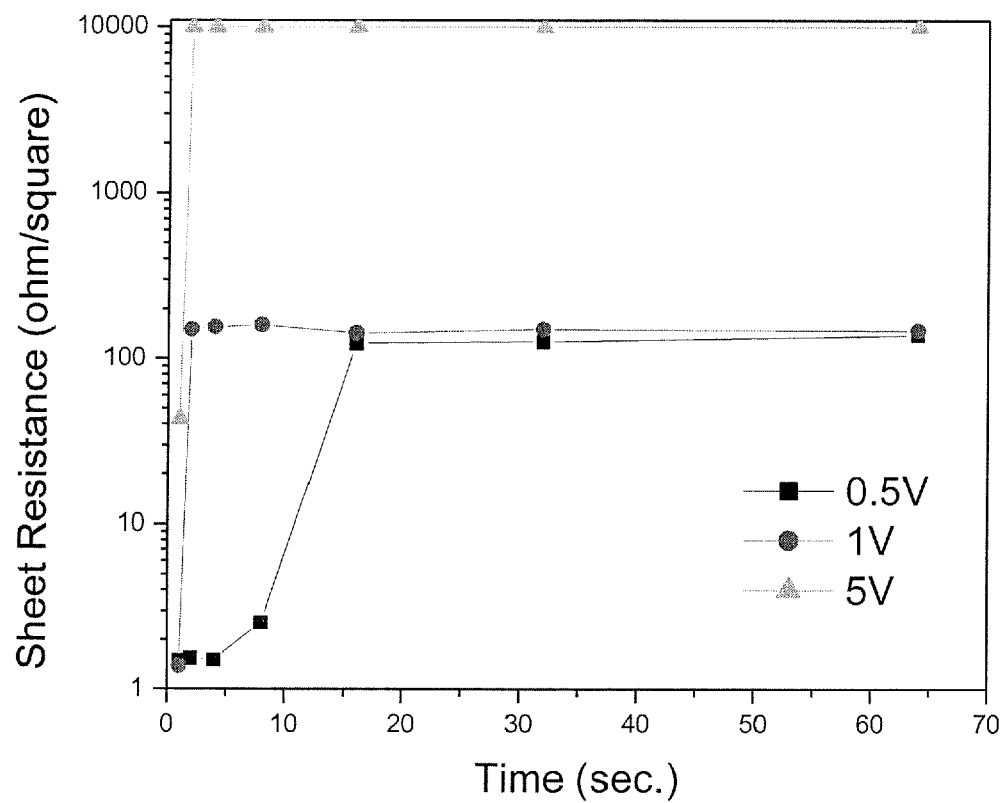
FIG. 8 shows a plot of sheet resistance of anodized AgCl films in accordance with embodiments of the present invention measured with a four point probe resistance measurement system as a function of anodizing bias.

The 4-point probe sheet resistance measurements for the anodized Ag/AgCl thin films were conducted with a Veeco FRR-100 system. Solid tungsten carbide tips were used and the contact tips were separated by 0.125 cm. The Ag thin films were grown large area Si wafers, then anodized with the same conditions as described with respect to the above device fabrication. For the films anodized at 5V, the AgCl grains were separated from each other, as shown in the FIG. 7, and the sheet resistance measurements hit the compliance of the system except for the films anodized after 1 sec., as shown in FIG. 8. Some residual Ag may remain on the surface of the Si substrate. The sheet resistances of AgCl films anodized at 0.5 and 1V reached a saturated sheet resistance around 150 ohm/□. These were consistent with the results shown in the FIG. 7, where the grain size of AgCl films anodized at 0.5 and 1V were very similar and the AgCl film was continuous for both cases. In the beginning of the anodization, the sheet resistances were lower for both conditions due to the existence of very conductive un-anodized Ag layer beneath the anodized AgCl layer.

Accordingly, a selective area AgCl anodization process can be implemented to provide a chloride recognition layer on a gate region of a HEMT. In addition, the effects of anodization bias voltage and time were studied. Based on the example experiments, a continuous anodized AgCl film was achieved with the bias voltage of 0.5 V-1 V. The AgCl films anodized at 5 V was not continuous and larger grain size was obtained. This anodization procedure can be integrated with the fabrication of a HEMT sensor.

In summary, The HEMT source-drain current showed a clear dependence on the chlorine concentration. In addition, for the experiments, the limit of detection achieved was $1\times10^{-8}$ M using a 20 μm×50 μm gate sensing area.

Accordingly, Ag/AgCl gated HEMTs, prepared by potentiostatic anodization in the solution of HCl in accordance with certain embodiments of the present invention, provide rapid changes in their drain currents depending on the concentrations of Cl⁻ ion solution.

What is claimed is:

1. A chloride sensor, comprising:
a high electron mobility transistor (HEMT); and
a chloride recognition layer on a gate region of the HEMT, wherein one side of the chloride recognition layer faces a channel of the HEMT below the gate region, and the other side is exposed for sensing chloride molecules, the HEMT being exposed for sensing chloride via the chloride recognition layer.

2. The chloride sensor according to claim 1, wherein the chloride recognition layer comprises metal chloride.

3. The chloride sensor according to claim 2, wherein the metal chloride comprises silver-chloride.

4. The chloride sensor according to claim 3, wherein the HEMT further comprises a titanium thin film electrode on the gate region and a silver thin film on the titanium thin film, wherein the silver chloride is provided on the silver thin film through potentiostatic anodization.

5. The chloride sensor according to claim 1, wherein the chloride recognition layer comprises indium nitride.

6. The chloride sensor according to claim 1, wherein the HEMT comprises an AlGaN/GaN HEMT.

7. The chloride sensor according to claim 1, wherein the HEMT comprises an AlGaAs/GaAs HEMT.

8. The chloride sensor according to claim 1, wherein the HEMT comprises an InGaP/GaAs HEMT.

9. The chloride sensor according to claim 1, wherein the HEMT comprises an InAlAs/InGaAs HEMT.

10. A method of detecting chloride, comprising:
providing, in contact with a fluid under test, a high electron mobility transistor (HEMT) chloride sensor comprising a chloride recognition layer on a gate region of the HEMT, wherein one side of the chloride recognition layer faces a channel of the HEMT below the gate region, and the other side is exposed for sensing chloride molecules, the HEMT being in contact with the fluid under test via the chloride recognition layer, wherein the chloride recognition layer causes the drain current of the HEMT to increase upon exposure to chloride.

11. The method according to claim 10, wherein the chloride recognition layer comprises metal chloride.

12. The method according to claim 11, further comprising:
resetting the chloride sensor by rinsing a surface of the metal chloride with deionized water.

* * * * *

UNITED STATES PATENT AND TRADEMARK OFFICE
CERTIFICATE OF CORRECTION

| | |
|---|---|
| PATENT NO. | : 8,836,351 B2 |
| APPLICATION NO. | : 12/997163 |
| DATED | : September 16, 2014 |
| INVENTOR(S) | : Fran Ren and Stephen John Pearton |

Page 1 of 1

It is certified that error appears in the above-identified patent and that said Letters Patent is hereby corrected as shown below:

In the Specification

Column 1,
Line 9, "60/060,317   61/060,327" should read --61/060,327,--.

Column 8,
Line 14, "CF ion" should read --Cl⁻ ion--.

Signed and Sealed this
Thirty-first Day of March, 2015

Michelle K. Lee
*Director of the United States Patent and Trademark Office*

UNITED STATES PATENT AND TRADEMARK OFFICE
CERTIFICATE OF CORRECTION

PATENT NO. : 8,836,351 B2  
APPLICATION NO. : 12/997163  
DATED : September 16, 2014  
INVENTOR(S) : Fan Ren and Stephen John Pearton Page 1 of 1

It is certified that error appears in the above-identified patent and that said Letters Patent is hereby corrected as shown below:

In the Specification

Column 1,
Line 9, "60/060,317  61/060,327" should read --61/060,327,--.

Column 8,
Line 14, "CF ion" should read --Cl⁻ ion--.

This certificate supersedes the Certificate of Correction issued March 31, 2015.

Signed and Sealed this
Fifth Day of May, 2015

Michelle K. Lee
*Director of the United States Patent and Trademark Office*